United States Patent [19]
Wernicke et al.

[11] Patent Number: 5,299,569
[45] Date of Patent: Apr. 5, 1994

[54] TREATMENT OF NEUROPSYCHIATRIC DISORDERS BY NERVE STIMULATION

[75] Inventors: Joachim F. Wernicke, League City; Reese S. Terry, Jr., Houston, both of Tex.; Jacob Zabara, Philadelphia, Pa.

[73] Assignee: Cyberonics, Inc., Webster, Tex.

[21] Appl. No.: 695,420

[22] Filed: May 3, 1991

[51] Int. Cl.$^5$ .............................................. A61N 1/18
[52] U.S. Cl. .................................... 607/45; 128/731; 607/62; 607/118
[58] Field of Search ................ 128/421, 419 S, 419 C, 128/731

[56] References Cited

U.S. PATENT DOCUMENTS

| | | | |
|---|---|---|---|
| 3,850,161 | 11/1974 | Liss | 128/419 S |
| 3,918,461 | 11/1975 | Cooper | 128/422 |
| 4,709,700 | 12/1987 | Hyrman | 128/421 |
| 5,025,807 | 6/1991 | Zabara | 128/421 |

Primary Examiner—William E. Kamm
Assistant Examiner—Scott M. Getzow
Attorney, Agent, or Firm—O'Connor, Cavanagh, Anderson, Westover, Killingsworth & Beshears

[57] ABSTRACT

Method and apparatus for treating and controlling neuropsychiatric disorders including schizophrenia, depression, and borderline personality disorder by selectively applying a predetermined electrical signal to the patient's vagus nerve for stimulation thereof to alleviate the symptoms of the disorder being treated. The electrical signal may be applied continuously, periodically, or intermittently to the vagus nerve depending, in part, on the nature of the disorder being treated. In certain instances, the electrical signal is applied upon detection of an event indicative of onset of the disorder. In other instances, the electrical signal is selectively applied at will to the vagus nerve, such as by patient activation of the signal generator. Parameter values of the electrical signal including pulse width, output current, frequency, on time and off time, are selectively programmable.

19 Claims, 2 Drawing Sheets

TREATMENT OF NEUROPSYCHIATRIC DISORDERS BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating patients with neuropsychiatric disorders by application of such signals to the vagus nerve, using an implantable neurostimulating device. Specifically, the invention is directed toward treating the symptoms of neuropsychiatric disorders such as schizophrenia, depression, and borderline personality disorder, by selective modulation of vagus nerve activity.

Schizophrenia was initially thought to have only psychological origins. Advances in psychobiology and psychopharmacology have revealed that the illness is primarily organic in nature. Electrophysiologic studies of patients with schizophrenia have supported an organic etiology. Although not entirely consistent, electroencephalogram (EEG) studies have tended to reveal abnormalities in these patients. Also, some parallels have been found between schizophrenia and epilepsy.

In *Psych. Res.* ((1989) 29:419-420, Meuller reported finding increased beta (17.5 Hz) wave activity over the left central-temporal region during acute psychotic episode, whereas before and after the episode the frequency distribution in the EEG was normal. Williamson et al. in *Can. J. Psych.* (1989) 34:680-686, reported that a review of EEG mapping studies revealed that abnormalities exist, with some studies finding asymmetric fast activity while others reported primarily slowing. In *Comprehensive Psych.* (1990) 30(1):34-47, Keshaven et al. reported that sleep EEG studies in schizophrenic patients consistently showed abnormalities, and that although not specific to schizophrenia, patients tended to show impaired sleep continuity and reduced total sleep, but not all patients showed these abnormalities.

Gruzelier et al. reported in *Int. J. Psychophysiol.* (1990) 8:275-282, that in normal subjects the power of the beta II region of the EEG spectrum is decreased in cortical areas associated with specific mental tasks, this focal reduction in power being consistent with the thalamocortical EEG desynchronization response, and being decreased or absent in patients with schizophrenia. In *Psychopathol.* (1989) 22:65-140, Diehl indicated that acute psychotic episodes may be manifestations of temporal lobe epilepsy, and expressed the belief that disorders may exist in the ictal as well as the interictal phase. Kido et al. discussed six patients with seizures followed by schizophrenia-like states, in *Japan J. Psych. Neurol.* (1989) 43:433-438. In *Intern. J. Neuroscience,* Ardilla et al. described three cases in which patients diagnosed as psychotic were actually found to have complex partial status epilepticus.

Turning to depressive disorder, developments in psychobiology and psychopharmacology have provided considerable evidence that major depressive disorder and bipolar depression are biological rather than psychological diseases. Deficiency of brain neurostimulators has been associated with depression. In particular, abnormally low concentrations of serotonin and its metabolites have been found in depressed patients, as reviewed by Stark et al. in *J. Clin. Psychopharmacol.* (1985) 46[3, Sec.2]:7-13. Several serotonin uptake inhibitors, which increase the amount of serotonin at the synapse have been shown to be effective antidepressants. Serotonin is a neurotransmitter known to be involved in the brain stem projections of the vagus nerve in animals (Kilpatrick et al. in *Eur. J. Pharmacol.* (1989) 159:157-164) and in humans (Reynolds et al. *Eur. J. Pharmacol.* (1989) 174:127-130). It is postulated, then, that increased activity of the vagus nerve would be associated with release of more serotonin in the brain.

The conclusion that depression has a biological basis is also supported by numerous electrophysiological and endocrine studies.

A paper by Pollock et al. in *Biol. Psychiatry* (1990) 27:757-780, reported that a review of studies of the EEG in awake depressed patients reveals that alpha and beta activity are increased compared to controls. Elevations of delta and theta frequency ranges were possibly present as well. It was also felt that increased beta activity may be particularly prominent in patients with coexistent anxiety. Buysee et al. reported in *Arch. Gen. Psych.* (1988) 45:568-575, finding that sleep EEG of patients with primary depression and secondary dementia showed a higher percentage of rapid eye movement (REM) and more phasic REM activity and intensity than patients with primary dementia and secondary depression.

A strong relationship has been found to exist between sleep and depression. One of the most effective treatments for depression is sleep deprivation, which, however, is not a practical long term therapy. As with schizophrenia, a relationship also appears to exist between depression and seizures.

A substantial body of data suggests that anti-convulsant compounds have a spectrum of therapeutic efficacy in a variety of psychiatric syndromes which have not been associated with an epileptoid process. Pathological degrees of neuronal excitability and/or dysregulation may be associated with marked alterations in behavior, which are potentially treatable with anticonvulsant compounds, even in the absence of a concurrent seizure disorder.

The use of electroconvulsive therapy (ECT) to induce seizures is a primary treatment in acute depressive disturbances. ECT appears equal or superior to traditional psychopharmacological treatment modes with tricyclic antidepressants. Although the precise mechanism by which the effect of ECT is achieved is not fully known, it is thought to be related to biochemical changes in the brain resulting from synchronous discharges associated with seizures. Antidepressant drugs may produce similar changes but without inducing seizures.

Certain anticonvulsant agents such as carbamazepine are used in psychiatric disorders. Some studies have indicated dramatic improvement by carbamazepine in affective and schizophrenia-like syndromes associated with epilepsy. Non-epileptic patients with nonspecific EEG abnormalities who suffer from marked psychiatric disorders have also been shown to respond favorably to this drug. In this group, improvements in violent behavior, irritability, emotional lability, depression, agitation, and apathy have been reported. Anticonvulsant compounds thus appear to have an important spectrum of clinical activity in neuropsychiatric syndromes in addition to their clinical utility in the treatment of epileptic disorders.

Borderline personality disorder is a poorly understood, but recognized psychiatric disorder which seems to have some overlap of schizophrenia and depression. Patients tend to be poorly functional without florid psychosis or overt depression. Lahmeyer et al reported, in *J. Clin. Psych.* (1989) 50(6):217-225, that sleep architecture in patients with borderline personality disorder is disturbed in that REM latency is decreased and REM density is increased. This was found to be particularly true if patients suffered coexisting depression, a history of affective illness or a family history of psychopathology. Sleep abnormalities were reported to appear similar to those seen in affective disorders.

In addressing a therapy involving nerve stimulation to treat such neuropsychiatric disorders, observation should be made of existing knowledge that most nerves in the human body are composed of thousands of fibers, having different sizes designated by groups A, B and C, carrying signals to and from the brain and other parts of the body. The vagus nerve, for example, may have approximately 100,000 fibers (axons) of the three different types, each of which carries such signals. Each axon of that nerve only conducts in one direction, in normal circumstances. The A and B fibers are myelinated, that is, they have a myelin sheath in the form of a substance largely composed of fat. On the other hand, the C fibers are unmyelinated.

Myelinated fibers are typically larger, have faster electrical conduction and much lower electrical stimulation thresholds than the unmyelinated fibers. Along with the relatively small amounts of electrical energy needed to stimulate the myelinated fibers, it is noteworthy that such fibers exhibit a particular strength-duration curve in response to a specific width and amplitude of stimulation pulse.

The A and B fibers are stimulated with relatively narrow pulse widths, from 50 to 200 microseconds ($\mu s$), for example. A fibers exhibit slightly faster electrical conductivities than the B fibers, and slightly lower electrical stimulation thresholds. The C fibers are relatively much smaller, conduct electrical signals very slowly, and have high stimulation thresholds typically requiring wider pulse widths (e.g., 300-1000 $\mu s$) and higher amplitudes for activation. Although the A and B fibers may be selectively stimulated without also stimulating the C fibers, the magnitude and width of the pulse required for stimulating the C fibers would also activate A and B fibers.

Although electrical stimulation of the nerve fiber typically activates neural signals in both directions (bi-directionally), selective unidirectional stimulation is achievable through the use of special nerve electrodes and stimulating waveforms. As noted above, each axon of the vagus nerve normally conducts in only one direction.

In a paper on the effects of vagal stimulation on experimentally induced seizures in rats (*Epilepsia* 1990, 31 (Supp 2): S7-S19), Woodbury has noted that the vagus nerve is composed of somatic and visceral afferents (i.e., inward conducting nerve fibers which convey impulses toward a nerve center such as the brain or spinal cord) and efferents (i.e., outward conducting nerve fibers which convey impulses to an effector to stimulate it and produce activity). The vast majority of vagal nerve fibers are C fibers, and a majority are visceral afferents having cell bodies lying in masses or ganglia in the neck. The central projections terminate, by and large, in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

Woodbury further notes that stimulation of vagal nerve afferent fibers in animals evokes detectable changes of the EEG in all of these regions, and that the nature and extent of these EEG changes depends on the stimulation parameters. Chase, in *Exp Neurol* (1966) 16:36-49, had also observed that vagal activation can affect the EEG activity of certain parts of the brain. The applicants herein postulate that synchronization of the EEG may be produced when high frequency ($>70$ Hz) weak stimuli activate only the myelinated (A and B) nerve fibers, and that desynchronization of the EEG occurs when intensity of the stimulus is increased to a level that activates the unmyelinated (C) nerve fibers. Woodbury also observes that vagal stimulation can produce widespread inhibitory effects on seizures and certain involuntary movements.

Extra-physiologic electrical stimulation of the vagus nerve has previously been proposed for treatment of epilepsy and various forms of involuntary movement disorders. Specifically, in U.S. Pat. No. 4,702,254 issued Oct. 27, 1987 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve in particular.

The NCP disclosed in the '254 patent may be activated either manually or automatically, to provide treatment for the duration of the seizure. Manual activation is performed when the patient experiences the aura at onset of the seizure. Alternatively, automatic activation may be triggered upon detection of instantaneous changes in certain state parameters immediately preceding or at onset of a seizure. Additionally, a prophylactic or preventive mode may be employed in which the NCP is activated periodically to reduce the occurrence and/or the intensity of the seizures. The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

It is a principal object of the present invention to apply the techniques of selective modulation of vagus nerve electrical activity, using a neurostimulator device which may be implantable, or used external to the body with only a small portion of the circuitry implanted or with only the nerve electrode(s) and associated lead(s) implanted percutaneously in the body, to the treatment of neuropsychiatric disorders including schizophrenia, depression, and borderline personality disorder.

SUMMARY OF THE INVENTION

The present invention is directed to methods and devices for treating and controlling certain neuropsychiatric disorders by selective stimulation of the vagus nerve (the tenth cranial nerve) in a predetermined manner primarily to synchronize or desynchronize the patient's EEG, depending on the specific nature of the disorder, to alter the serotonin concentration in the brain, and to improve the patient's sleep patterns. In general, a normal EEG displays low voltage and relatively fast activity. Situations do occur in which the EEG activity slows down, such as during sleep, and displays higher voltage, but this is normal.

The apparatus of the invention employs a neurostimulator (preferably but not necessarily implantable) to selectively apply the therapy to treat the specific neuropsychiatric disorders which may include schizophrenia, depression, borderline personality disorder, or other related disorders. The therapy is delivered in a manner to modulate the vagal activity of the patient in a predetermined manner to treat and relieve the symptoms of the disorder, although it would not necessarily be expected to be effective in alleviating the underlying root cause of the disorder. The neurostimulator is programmed by the attending physician to provide the desired therapeutic modality for treatment of the specific neuropsychiatric disorder suffered by the patient.

We have concluded that vagal stimulation can be effective for treating schizophrenia, for example. One observation toward that conclusion is that fast desynchronous (beta) activity and paroxysmal (synchronous) activity of the EEG have both been reported in studies of this disorder. At some stimulation parameters, vagal stimulation will synchronize the EEG, with a resultant beneficial effect on treatment of the disorder where increased beta wave activity is present. A second observation is the apparent relationship between schizophrenia and temporal lobe epilepsy. The temporal lobes are part of the limbic system, which, we postulate, is malfunctioning in patients with schizophrenia. Vagal stimulation can suppress temporal (complex partial) seizures, which are generated in the limbic system. The structures of this system are interconnected, and the beneficial effect of vagal stimulation seen in the temporal lobes may be transmitted to other brain structures, leading to a similar effect on schizophrenia. In this case, the abnormality being treated is a synchronous paroxysmal (epileptiform) discharge, and the therapy is designed to desynchronize the EEG.

Selection among various strategies for vagal modulation to treat the specific neuropsychiatric disorder will depend on a number of factors. These include (i) a consideration of which of the nerve fibers are to be subjected to the modulation; (ii) the modality for achieving synchronization or desynchronization of the EEG; (iii) the modality for effecting a change in the serotonin concentration of the brain; (iv) whether some type of physiologic signal is generated which can be detected and employed to trigger the modulation; and/or (v) whether a "carryover" or refractory period occurs after modulation in which the benefit of the modulation is maintained. Although these are not all of the factors to be considered for selecting a stimulation strategy for treatment of a particular disorder, nor necessarily listed in order of importance, they are indicative of considerations which may apply in a specific case.

In the treatment, the invention uses different signal parameters and threshold curves to activate the various fibers of the patient's vagus nerve for selective modulation thereof. By appropriately setting pulse width and amplitude of the electrical signal to be delivered by the neurostimulator to the patient's vagus nerve, the nerve fibers can be selectively stimulated, such as A and not B and C; or A and B, but not C; or A, B and C. Various related factors, however, must be considered in the selection process. For example, because the C fibers conduct signals very slowly, they are not highly responsive to techniques of fast stimulation. Therefore, if it were desired to increase desynchronous activity of the EEG by stimulation of the C fibers at 50 Hz, for example, for treatment of a particular neuropsychiatric disorder, it would be prudent to use a short pulse train for the stimulus. This is because the fibers would become refractory to the stimulation within a relatively short time interval and thus incapable of tracking the pattern of a longer train. After a suitable recovery period, another short pulse train may be applied to achieve further treatment. The precise pattern to be used, e.g., the length of the time intervals on and off, will depend upon and be adjusted to the individual patient and the particular disorder being treated.

Furthermore, proper designation of amplitude and frequency range of the applied signals allows tuning of the fibers for EEG synchronization or desynchronization, by which additional control is achieved for the particular disorder to be treated. Desynchronization of the EEG has been found to be achieved by stimulation at frequencies in the range from 20 to 75 Hz at levels above 0.1 volt, but requires signals greater than 3 volts at frequencies above 75 Hz. If the frequency is above 75 Hz and the signal is below 3 volts, EEG synchronization is achieved. The actual voltage required depends on the type and geometry of the electrode and the impedance of the electrode-tissue interface.

According to the invention, the basic stimulation strategy calls for modulating the activity of a number of brain structures, including the limbic system, the reticular formation, and the hippocampus. As described by Rutecki in Epelipsia (1990) 31 (Supp. 2): S1-S6, the vagus nerve projects directly or indirectly to these brain structures. Preferably, this strategy is implemented by circadian programming to automatically activate the stimulus generator to continuously, periodically or intermittently generate an electrical signal appropriate for application to the patient's vagus nerve to modulate the activity of the brain structures including limbic system, reticular formation and hippocampus. For example, if epileptiform activity is being treated the modulation is effected to desynchronize the synchronous high voltage slow wave, and increase the background desynchronous activity. In another aspect of the invention, the treatment is carried out by applying the selectively modulating electrical signals to the patient's vagus nerve in response to the occurrence of one or more predetermined detectable events.

In the case of depression, although sleep deprivation is not a practical long term therapy, vagal stimulation can alter sleep state architecture and is a modality that can produce a beneficial antidepressant effect. Also, the relationship between seizures and depression, and the effectiveness of treating depression (major depressive disorder) with ECT may be useful for the prescription of vagus nerve stimulation. ECT demonstrates the effectiveness of brain electrical stimulation in the therapy of psychiatric disorders, but the electric current delivered to the brain is sufficiently intense to produce seizures in the patients. In contrast, treatment delivered by the neurostimulator according to the method and apparatus of the present invention is inherently safer and more comfortable for the patient than ECT. The output current is considerably smaller and is not applied directly to the brain through the skull. It appears that certain stimulation parameters for the vagus nerve produce synchronization of brain activity which leads to the biochemical changes required to relieve depression, but without causing seizures. Similar biochemical changes may be achieved with antidepressant drugs. Serotonin, one of the neurotransmitters affected by antidepressant drugs, is also involved in mediation of vagal impulses.

It further appears that vagal stimulation can be effective in the treatment of borderline personality disorders, at least because of the abnormalities in sleep architecture attendant with such disorders and the capability of vagal stimulation to alter sleep states.

Broadly, then, the present invention is directed to apparatus and methods which employ a neurostimulator device, preferably implantable, for therapy or treatment of any of several types of neuropsychiatric disorders through nerve stimulation. The modulating signals applied to the vagus nerve may stimulate or inhibit other neural signals to produce excitatory or inhibitory neurotransmitter release, but for purposes of this disclosure both situations are included within the term "stimulating". It should be emphasized that although the preferred nerve site for application of the modulating signals is the vagus nerve, effective treatment may be achieved through application of the stimulus to one or more other nerves, particularly among the cranial nerves, and such treatment is deemed to be within the ambit of the present invention. The invention recognizes and employs specific techniques of vagal stimulation in a therapeutic regimen for treatment of the particular neuropsychiatric disorder.

Accordingly, it is a more specific object of the invention to provide methods and apparatus for treating and controlling neuropsychiatric disorders by applying electrical stimuli to the patient's vagus nerve or other cranial nerve, to activate a specific group of fibers from among all of the fiber groups of the selected nerve(s), and to selectively synchronize or desynchronize the patient's EEG and/or to vary REM activity according to the specific nature of the disorder, and/or to alter brain serotonin concentrations.

Another object of the invention is to provide methods of treating and controlling neuropsychiatric disorders by sensing a symptom of the disorder or the occurrence of a predetermined detectable event and thereafter automatically or manually effecting modulation of vagal activity through the application of preselected stimuli to the patient's vagus nerve to suppress the disorder.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which.

DESCRIPTION OF THE PRESENTLY PREFERRED EMBODIMENT AND METHOD

Figure 1:
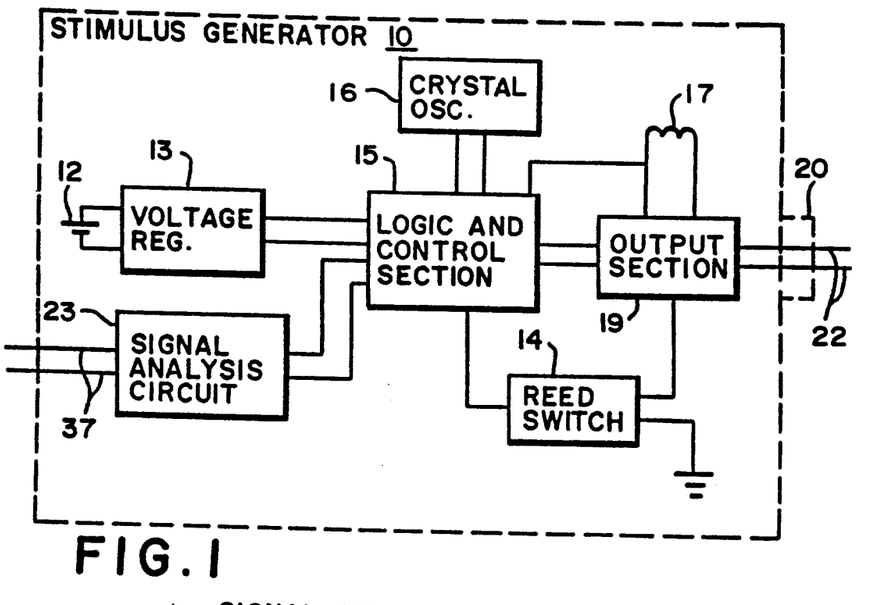
FIG. 1 is a simplified block diagram of an implantable neurostimulator electronics package (stimulus generator) for use (with appropriate parameter settings and ranges) in treating neuropsychiatric disorders according to the present invention.
Figures 2, 3:
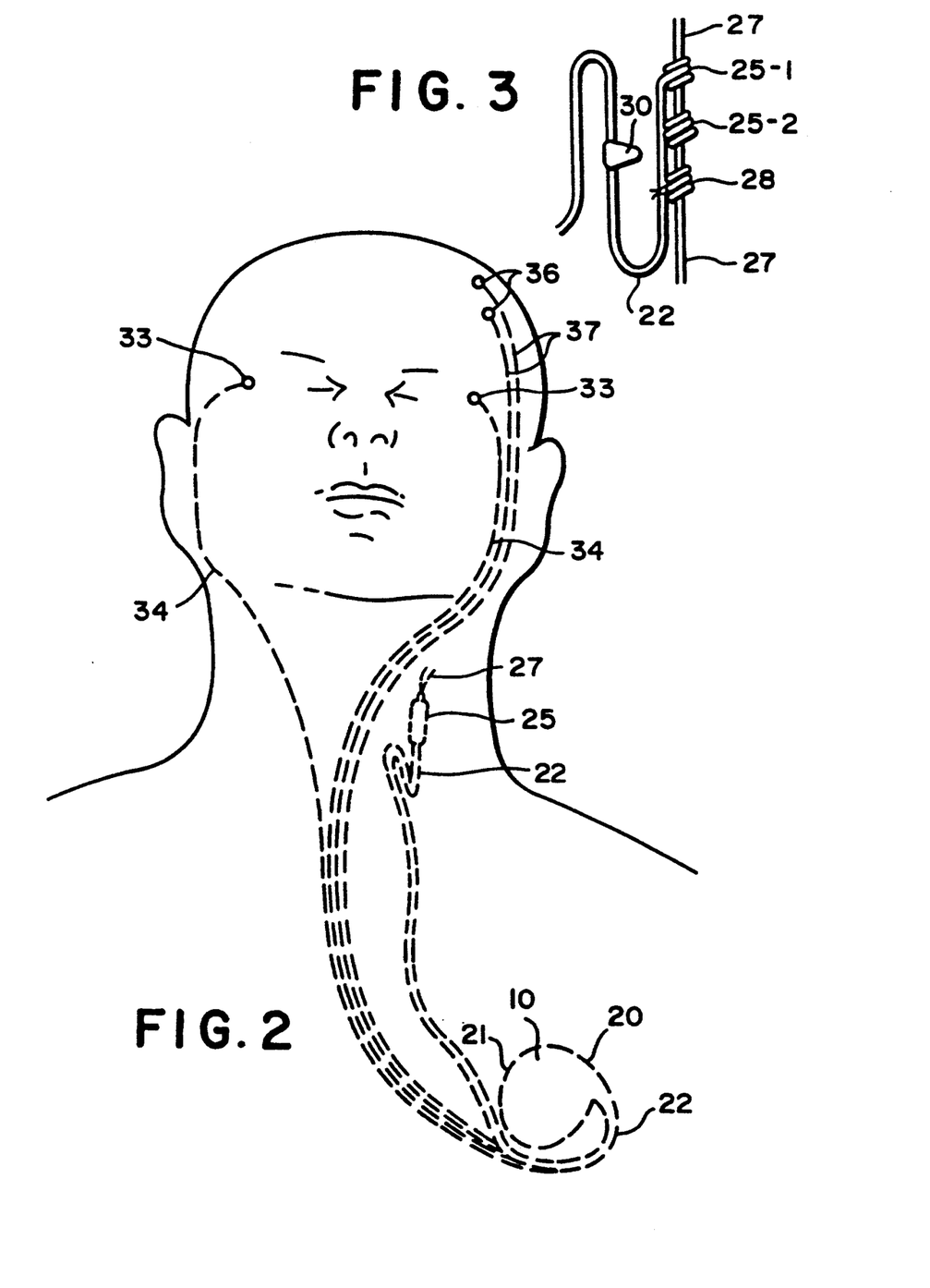
FIG. 2 is a simplified fragmentary illustration of a preferred embodiment of the stimulus generator and lead/electrode system of the neurostimulator implanted in the patient's body.
FIG. 3 is a detailed fragmentary illustration of the nerve electrode as implanted on the vagal nerve in the neck of the patient for modulating vagal activity.

Referring now to the drawings, a block diagram of the basic components of the stimulus generator of a neurostimulator and their interrelationship is illustrated in FIG. 1 and further details of location of an implantable version of the device and the associated lead/electrode system are shown in FIGS. 2 and 3. A generally suitable form of neurostimulator for use in the apparatus of the present invention is disclosed in copending U.S. patent application Ser. No. 07/434,985, now U.S. Pat. No. 5,154,172, issued Oct. 13, 1992, to Anthony J. Varrichio et al., titled "Current Source with Programmable Overhead VOltage", filed Nov. 10, 1989 (referred to herein as the '985 application"), assigned to the same assignee as the instant application. The specification of the '985 application is incorporated herein in its entirety by reference, but certain portions of it are summarized in this application for the sake of convenience to the reader.

The neurostimulator utilizes a conventional microprocessor and other standard electrical and electronic components, and in the case of an implanted device, communicates with a programmer and/or monitor located external to the patient's body by asynchronous serial communication for controlling or indicating states of the device. Passwords, handshakes and parity checks are employed for data integrity. The neurostimulator also includes means for conserving energy, which is important in any battery operated device and especially so where the device is implanted for medical treatment of a disorder, and means for providing various safety functions such as preventing accidental reset of the device.

The stimulus generator 10 (FIG. 1) is preferably adapted to be implantable in the patient's body, in a pocket formed by the surgeon just below the skin in the chest as shown in FIG. 2, although a primarily external neurostimulator may alternatively be employed. The neurostimulator also includes implantable stimulating electrodes (described below) together with a lead system 22 for applying the output signal of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand and the computer. The external components of the system are not shown in the drawings.

In conjunction with its microprocessor-based logic and control circuitry, the stimulus generator 10 or other implanted or external circuitry may include detection circuitry for sensing an event indicative of an abnormality to trigger automatic delivery of the stimulating signal. For example, surface or depth electrodes may be implanted to sense specific characteristics of the patient's EEG for triggering the therapy, as will be discussed presently in conjunction with the description of FIGS. 2 and 5. However, this involves complex and delicate electrode/lead implantation procedures as well as the requirement of circuitry for spectral analysis and/or programmable spectral or pattern recognition. Preferably, therefore, the treatment is applied continuously, periodically or intermittently or in accordance with the patient's circadian rhythm. The stimulus generator is designed, implemented and programmed to deliver a selectively patterned stimulating signal to modulate vagal activity in a manner designed to treat the specific neuropsychiatric disorder of interest.

As shown in FIG. 1, stimulus generator 10 includes a battery (or set of batteries) 12, which may be of any reliable long-lasting type conventionally employed for powering implantable medical electronic devices (such as batteries employed in implantable cardiac pacemakers or defibrillators). In the preferred embodiment of the stimulus generator, the battery is a single lithium thionyl chloride cell. The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device. Among these programmable functions are output current, output signal frequency, output signal pulse width, output signal on-time, output signal off-time, daily treatment time for continuous or periodic modulation of vagal activity, and output signal-start delay time. Such programmability allows the output signal to be selectively crafted for application to the stimulating electrode set (FIGS. 2 and 3) to obtain the desired modulation of vagal activity for treatment and control of the disorder. Timing signals for the logic and control functions of the generator are provided by a crystal oscillator 16. A magnetically-actuated reed switch 14 may be incorporated in the electronics package to provide the generator with manual activation capability (by use of an external magnet, not shown, placed immediately adjacent to the package or its implant site).

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

Logic and control section 15 of the stimulus generator 10 controls an output circuit or section 19 which generates the programmed signal levels appropriate to the disorder being treated. The output section and its programmed output signal are coupled (directly, capacitively, or inductively) to an electrical connector 20 on the housing 21 of the generator and to lead assembly 22 connected to the stimulating electrodes (FIGS. 2 and 3). If EEG sensing electrodes or eye movement sensing electrodes are to be implanted in the patient for triggering delivery of therapy by the stimulus generator on detection of an event indicative of the neuropsychiatric disorder of interest, a sense signal analysis circuit 23 is provided within the generator housing 21, with connections to the microprocessor in logic and control section 15 and to the sensing electrodes. An exemplary sense signal analysis circuit will be described presently.

Housing 21 in which stimulus generator 10 is encased is hermetically sealed and composed of a material such as titanium which is biologically compatible with the fluids and tissue of the patient's body. Further details of suitable structure and operation of the neurostimulator, beyond those by which the device is adapted to treat the neuropsychiatric disorder as described herein, are available in the '985. application, to which the reader is referred. Although not used in the preferred embodiment, if a detection system is employed with the neurostimulator to detect characteristics of the EEG, or to detect eye movement, by which to initiate the vagal stimulation automatically upon sensing the predetermined event indicative of need for treatment, the signal parameters of the implanted device may be calibrated by telemetry (via the programming wand) to the particular patient and the results then programmed into the microprocessor for the appropriate treatment.

FIG. 2 illustrates the preferred location of implanted generator 10, in case 21 with connector 20, in the patient's chest in a cavity formed by the implanting surgeon just below the skin, much as a pacemaker pulse generator would be implanted. A stimulating nerve electrode set 25 (FIG. 3) is conductively connected to the distal end of insulated electrically conductive lead assembly 22 which is attached at its proximal end to connector 20. Electrode set 25 is a bipolar stimulating electrode, preferably of the type described in U.S. Pat. No. 4,573,481 issued Mar. 4, 1986 to Bullara. The electrode assembly is surgically implanted on the vagus nerve 27 in the patient's neck. The two electrodes 25-1 and 25-2 are wrapped about the vagus nerve, and the assembly is secured to the nerve by a spiral anchoring tether 28 preferably as disclosed in U.S. Pat. No. 4,979,511 issued Dec. 25, 1990 to Reese S. Terry, Jr. and assigned to the same assignee as the instant application. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

Eye movement sensing electrodes 33 may be implanted at or near the outer periphery of each eye socket in a suitable location to sense muscle movement or actual eye movement, as shown in FIG. 2, and electrically connected to leads 34 implanted via a catheter or other suitable means (not shown) and extending along the jawline through the neck and chest tissue to the sense signal analysis circuit 23 of stimulus generator 10. Sense electrodes 33 are utilized for rapid eye movement (REM) detection in a pattern indicative of the disorder to be treated, as will be described in greater detail below. Alternatively, or additionally, EEG sense electrodes 36 may be implanted in spaced apart relation through the skull, and connected to leads 37 implanted and extending along the scalp and temple and then along the same path and in the same manner as described above for the eye movement electrode leads. These or other types of sensing electrodes would only be required for alternative embodiments of the invention, since the preferred embodiment utilizes a continuous, periodic or intermittent stimulus signal applied to the vagus nerve (each of which constitutes a form of continual application of the signal), appropriate to treat the particular neuropsychiatric disorder which has been diagnosed in the case of the specific patient under observation.

The stimulus generator may be programmed with an IBM-compatible personal computer (not shown) using programming software of the type copyrighted by the assignee of the instant application with the Register of Copyrights, Library of Congress, or other suitable software based on the description herein, and a programming wand (not shown). The wand and software permit noninvasive communication with the generator after the latter is implanted. The wand is preferably powered by internal batteries, and provided with a "power on" light to indicate sufficient power for communication. Another indicator light is preferably provided to show that data transmission is occurring between the wand and the generator.

Figure 4:
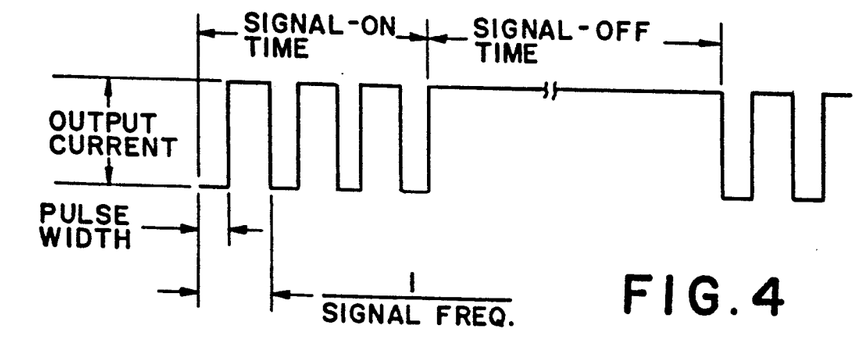
FIG. 4 is an illustrative idealized electrical output signal waveform of the stimulus generator useful for clarifying relevant parameters of the signal developed by the stimulus generator for application to the nerve.

The operation of stimulus generator 10 to control and treat the neuropsychiatric disorder of interest will be described with reference to FIG. 4, which illustrates the general nature, in idealized representation, of the output signal waveform delivered by output section 19 of the neurostimulator to electrode assembly 25. This illustration is presented principally for the sake of clarifying terminology, including the parameters of output signal on-time, output signal off-time, output signal frequency, output signal pulse width, and output signal current.

In the treatment of schizophrenia according to the invention, the preferred stimulation strategy is to use circadian programming to desynchronize the EEG during the patient's normal waking hours, and to synchronize the EEG at night to improve sleep. Alternatively, detection strategies such as EEG detection of beta waves over the central temporal region, and/or of abnormal sleep patterns may be employed to trigger the stimulation. In the preferred embodiment and method, the vagal stimulation is continuously, periodically, or intermittently performed during prescribed segments of the patient's circadian cycle. For example, daytime stimulation may be periodic with a random frequency for the stimulating pulse waveform, with parameter selection for EEG desynchronization; and nighttime stimulation may employ a periodically applied pattern with parameters selected to synchronize the patient's EEG (e.g., at 90 Hz, 1 mA, 0.10 ms for the pulse waveform), alternating with desynchronizing stimuli at predetermined intervals (e.g., 100 minute separation) to produce low voltage fast (REM) activity. Such a regimen of vagal stimulation is programmed into the neurostimulator electronics package.

The schizophrenic patient is generally unable to recognize the symptoms of the disorder, and consequently no provision is made for patient activation of the neurostimulator for treatment of this particular disorder. However, the stimulus generator may be implemented for manual activation by a companion of the patient (using, for example, an external magnet to actuate the reed switch 14, in the implantable device of FIG. 1).

The preferred range of stimulation parameters for treatment of schizophrenia and the typical value of each parameter of the stimulating output signal are as follows:

|  | Range | Desynch, Typical | Synch, Typical |
| --- | --- | --- | --- |
| Pulse Width | 0.05–1.5 ms | 0.5 ms | 0.1 ms |
| Output Current | 0.1–5.0 mA | 1.5 mA | 1.5 mA |
| Frequency | 5–150 Hz | 25 Hz | 80 Hz |
| On Time | 5–500 sec | 300 sec | 30 sec |
| Off Time | 5–500 sec | 10 sec | 5 sec |
| Frequency sweep | 10–50 Hz | Optional | |
| Random frequency | 10–50 Hz Daytime Only | Optional | |

Another activation modality for daytime stimulation is to program the output of the neurostimulator pulse generator to the maximum amplitude which the patient can tolerate, with cycling on and off for a predetermined period of time followed by a relatively long interval without stimulation.

For treating depression, the preferred stimulation strategy of the invention is to employ circadian programming for night time stimulation to increase REM activity, and increase synchronization of the EEG during the patient's normal waking hours. Alternatively, a strategy may be employed for EEG detection of alpha or beta waveforms, and/or EEG detection and analysis of REM activity during sleep at night, followed by large signal, infrequent stimulation when the neurostimulator generator is activated by the detection circuitry. Here again, such detection may be implemented using surface or depth sensing electrodes and EEG spectral or REM analysis circuitry.

The patient suffering from depression is capable of recognizing the symptoms of the disorder, and therefore may be provided with a neurostimulator which is implemented, in the manner described above, to permit manual activation for delivery of the therapy. In the case of manual activation, the therapy applied preferably would be that normally employed during the patient's waking hours, i.e., to synchronize the EEG. It is unlikely, however, that an antidepressant effect would be achieved quickly, since treatment of depression using drugs begins to take effect in from two to four weeks and is probably related to changes in receptors, and the use of vagal stimulation for depression is likely to produce a similar result. For that reason, the neurostimulator should be programmed to generate the stimulus for a relatively long period of time in response to manual activation.

As noted earlier herein, the treatment is designed, in part, to increase the activity of the vagus nerve by which to evoke a release of greater amounts of the neurotransmitter serotonin in the patient's brain. This alteration, and specifically an increase, of the serotonin concentration in the brain is the result of an enhancement of the production of this natural antidepressant through vagal modulation.

A preferred range of stimulation parameters to treat depression, and the typical value of each parameter of the stimulus generator programmed output signal are as follows:

|  | Range | Desynch, Typical | Synch, Typical |
| --- | --- | --- | --- |
| Pulse Width | 0.05–1.5 ms | 0.10 ms | 0.5 ms |
| Output Current | 0.1–5.0 mA | 1.0 mA | 1.5 mA |
| Frequency | 5–150 Hz | 90 Hz | 20 Hz |
| On Time | 5–500 sec | 30 sec | 300 sec |
| Off Time | 5–500 sec | 30 sec | 10 sec |
| Frequency sweep | 10–50 Hz | Optional | |
| Random frequency | 10–50 Hz | Optional | |

The circadian programming may also be set for synchronization of sleep patterns at night (e.g., output stimulating signal of 20 Hz, 500 ms, and 2 mA, cycled at 300 seconds on and 30 seconds off).

An activation modality for daytime stimulation in which the stimulus is applied to the nerve at the maximum amplitude tolerable by the patient, with on/off cycling for a first interval followed by a relatively long second interval without stimulation, similar to a modality described above for treating schizophrenia, may have value for treating depression. It bears some analogy to ECT which has been found effective in cases of depression, and would produce synchronous activity of the EEG for the brief stimulation intervals.

In the treatment of borderline personality disorder, the preferred stimulation strategy is designed to modify the patient's sleep patterns toward a normal pattern. Here, a suitable detection strategy is to employ implanted electrodes to sense muscle movement or actual eye movement during sleep, such as are shown in FIG. 2, and to analyze the detected REM activity; or to perform EEG detection with surface or depth EEG electrodes, followed by spectral analysis of the EEG. Again, however, circadian programming of the output signal for automatic stimulation in continuous, periodic or intermittent patterns is preferred for the sake of avoiding additional invasive procedures. In general, patient activation of the neurostimulation generator is not a viable option for the patient suffering from borderline personality disorder, although here again the provision of manual activation means could be appropriate for use by a companion.

The preferred range of stimulation parameters for treatment of borderline personality disorder and the typical value of each parameter of the programmed stimulation signal are as follows:

|  | Range | Typical |
| --- | --- | --- |
| Pulse Width | 0.05–1.5 ms | 0.10 ms |
| Output Current | 0.1–5.0 mA | 1.0 mA |

-continued

|  | Range | Typical |
| --- | --- | --- |
| Frequency | 5–150 Hz | 90 Hz |
| On Time | 5–1500 sec | 30 sec |
| Off Time | 5–1500 sec | 10 sec |
| Frequency sweep | 40–100 Hz | Optional |
| Random frequency | 40–100 Hz | Optional |

The circadian programming may employ specific patterns at night to modify REM activity for the purpose of increasing REM latency and to decrease REM intensity, tailored for each individual patient. Such a regimen of stimulation is best designed where the patient exhibits historically consistent sleep patterns, and would require defining the stimulation pattern for discrete time block during the sleep period.

If sense electrodes are to be utilized to detect onset of the disorder being treated, the signal analysis circuit 23 is incorporated in the stimulus generator 10 (FIG.

Figure 5:
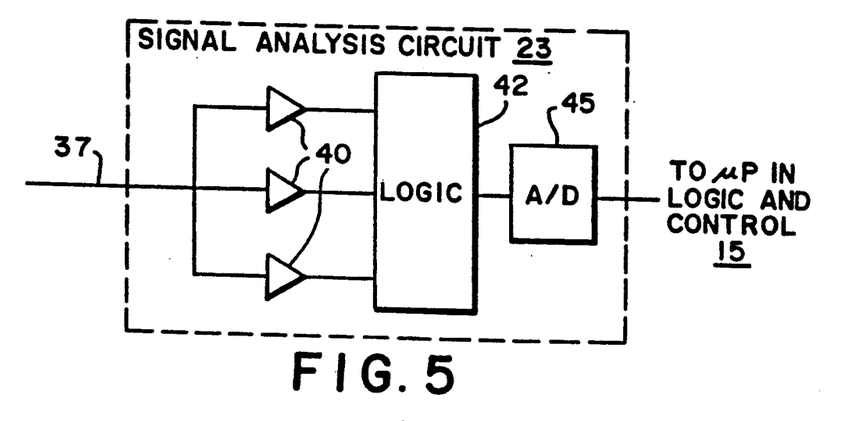
FIG. 5 is a simplified block diagram of an EEG signal analysis circuit used in the stimulus generator.

Referring to FIG. 5, where the sense electrodes are EEG electrodes such as 36 and associated leads 37 of FIG. 2, analysis circuit 23 is implemented for EEG detection and analysis. To that end, circuit 23 includes a plurality of parallel active sense signal bandpass filters 40 staged to provide selective filtering in the ranges from 0–2 Hz, 2–4 Hz and 15–20 Hz, for example; a logic circuit 42 to select the output of one filter from among the plurality of filters 40; and an analog/digital (A/D) converter 45. The outputs of the filters are individually sampled by the logic circuit 42, and the sampling rate, averaging time interval, and weighting assigned to each sense signal band, are controlled by the microprocessor in the logic and control section 15 of the stimulus generator 10 (FIG. 1), to detect the EEG pattern. Upon detection of the symptom of interest of the disorder being treated, the processed digital signal is supplied to the microprocessor to trigger application of the stimulating signal to the patient's vagus nerve.

The activation of the analysis circuit 23 and its internal component circuitry need not be continuous, but only periodic such as every few hours, depending on the disorder being treated.

Various features may be incorporated into the neurostimulator for purposes of the safety and comfort of the patient. For example, comfort would be enhanced by programming the output stimulus to ramp up during the first two seconds of stimulation, rather than to be delivered abruptly. Also, the implanted generator may be provided with a clamping circuit to limit the maximum voltage, to 14 volts for example, which is delivered to the vagus nerve. Such a maximum limit is designed to prevent damage to the patient's vagus nerve.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and messages to facilitate simple and rapid programming while keeping the user fully informed of everything occurring at each step of a sequence. Programming capabilities should include capability to modify the adjustable parameters of the stimulus generator and its output signal, to test device diagnostics, and to store and retrieve telemetered data. It is desirable that when the implanted unit is interrogated, the present state of the adjustable parameters is displayed on the monitor of external PC so that the programmer may then conveniently change any or all of those parameters at the same time; and, if a particular parameter is selected for change, all permissible values for that parameter are displayed so that the programmer may select an appropriate desired value for entry into the neurostimulator.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. The nerve electrodes are capable of indefinite use absent indication of a problem with them observed on the diagnostics testing.

Although a preferred embodiment of apparatus and certain preferred methods for treating and controlling neuropsychiatric disorders through vagal modulation according to the invention have been described herein, it will be apparent to those skilled in the field from a consideration of the foregoing description that variations and modifications of such embodiments, methods and techniques may be made without departing from the true spirit and scope of the invention. For example, although a totally implantable device is preferred, the electronic energization package may, if desired, be primarily external to the body. Stimulation can be achieved with an RF power device implemented to provide the necessary energy level. The implanted components may be limited to the lead/electrode assembly, a coil and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes. The disadvantages of such an implementation are that the external transmitter must be carried by the patient, greater power is required for activation, and the output current to the nerve is less stable.

An external stimulus generator may be employed with leads extending percutaneously to the implanted nerve electrode set. The major problem encountered with this technique is the potential for infection, but it is useful to allow short term testing of the patient to determine whether the particular neuropsychiatric disorder suffered by the patient under observation is amenable to successful treatment. If it is, a more permanent implant may be provided.

Accordingly, it is intended that the invention shall be limited only to the extent required by the appended claims and the rules and principles of applicable law.

What is claimed is:

1. A method of treating patients with neuopsychiatric disorders, which includes
   selecting a patient suffering form a neuropsychiatric disorder,
   determining the type of neuropsychiatric disorder exhibited by the patient, and
   selectively applying a predetermined electrical stimulus to the patient's vagus nerve for modulating the electrical activity thereof in a manner to alleviate the symptoms of the neuropsychiatric disorder exhibited by the patient being treated.

2. The method of claim 1, wherein the neuropsychiatric disorder being treated is schizophrenia, and
   the predetermined stimulus is an electrical signal in the form of a pulse waveform with signal parameters programmed to increase desynchronous activity of the patient's EEG during waking hours, and to increase synchronous activity of the EEG during sleep.

3. The method of claim 1, wherein the neuropsychiatric disorder being treated is one of schizophrenia, depression or a borderline personality disorder, and further including
   detecting an event indicative of onset of the disorder, and
   initiating application of the predetermined electrical stimulus upon such detection.

4. The method of claim 3, wherein the neuropsychiatric disorder being treated is schizophrenia, and
   the detected event is one of (i) EEG beta waves over the central temporal region and (ii) abnormal sleep patterns, of the patient.

5. The method of claim 3, wherein the neuropsychiatric disorder being treated is depression, and
   the detected event is one of (i) EEG alpha and beta waves, and (ii) predetermined level of REM activity during sleep, of the patient.

6. The method of claim 3, wherein the neuropsychiatric disorder being treated is borderline personality disorder, and
   the detected event is a predetermined level of REM activity during sleep by the patient.

7. The method of claim 1, wherein the neuropsychiatric disorder being treated in depression, and
   the predetermined stimulus is an electrical signal in the form of a pulse waveform with signal parameters programmed to increase synchronous activity of the patient's EEG during the patient's waking hours, and to increase the patient's rapid eye movement (REM) activity during sleep.

8. The method of claim 1, wherein
   the predetermined stimulus is an electrical signal selected to activate the patient's vagus never to modify the release of serotonin in the patient's brain.

9. The method of claim 8, wherein the neuropsychiatric disorder being treated is depression, and including
   applying the predetermined electrical stimulus to the patient's vagus nerve continually over a relatively long period of time to increase the release of serotonin.

10. The method of claim 1, wherein the neuropsychiatric disorders being treated is depression, including
    manually activating the predetermined stimulus as an electrical signal in the form of a pulse waveform with signal parameters programmed to alleviate symptoms of the depression.

11. The method of claim 1, wherein the neuropsychiatric disorder being treated is borderline personality disorder, and
    the predetermined stimulus is an electrical signal in the form of a pulse waveform with signal parameters programmed to increase the patient's REM latency and decrease REM intensity during sleep.

12. The method of claim 1, wherein
    said stimulus is an electrical signal in the form of a pulse waveform with programmable signal parameters, and is applied to a nerve electrode implanted in the patient's neck on the vagus nerve.

13. The method of claim 12, wherein
said electrical signal is further programmable for any of continuous periodic or intermittent application to the patient's vagus nerve.

14. The method of claim 12, wherein
said electrical signal is selectively applied at will to the patient's vagus nerve.

15. The method of claim 12, wherein
the parameter values of the electrical signal including pulse width, output current, frequency, on time and off time, are selectively programmable.

16. A new use for a neurostimulator device adapted to be implanted in a human patient, in which the device comprises an electrical signal generator which is programmable to generate an electrical output signal having selected signal parameters, and an electrical lead adapted to be connected at a proximal end thereof to the signal generator, the lead including an electrode electrically connected to a distal end of the lead and having a configuration for encompassing a portion of the length of a nerve so that the electrode is adapted to be implanted on the patient's vagus nerve to modulate the electrical activity of the nerve in response to application of the programmed electrical output signal from the signal generator to the lead, the new use of the neurostimulator device comprising the steps of:
 implanting said electrode on the vagus nerve of the patient,
 electrically connecting the proximal end of the lead to said signal generator,
 programming the output signal of the signal generator to constitute a pulse waveform with parameter values of pulse width, output current, frequency, and on and off times selected for therapeutic treatment and control of a neuropsychiatric disorder of the patient among the group of such disorders consisting of schizophrenia, depression, borderline personality disorder.

17. The new use of the neurostimulator device of claim 16, including:
 detecting an event indicative of onset of the neuropsychiatric disorder being treated, and, in response to such detected event, applying the output signal of the signal generator to the lead, so as to modulate the electrical activity of the vagus nerve to alleviate symptoms of the neuropsychiatric disorder being treated.

18. A method for use in advancing the treatment and control of neuropsychiatric disorders, including the steps of
 providing an electrical lead with a stimulating electrode assembly at its distal end for implantation on a patient's vagus nerve,
 providing a programmable stimulus generator for generating electrical pulse sequences with selectively variable electrical parameters for selective application to the lead/electrode assembly when implanted on the vagus nerve,
 incorporating an electrical connector in the stimulus generator to accommodate electrical connection of the proximal end of the electrical lead to the stimulus generator,
 restricting the programmable ranges of the variable parameters of the electrical pulse sequences to values which in combination will stimulate the vagus nerve and thereby modulate its electrical activity when one or more programmed pulse sequences are applied to the nerve via the lead/electrode assembly, to alleviate symptoms of the particular neuropsychiatric disorder to be treated,
 adapting the stimulus generator for physician control of the programming, and
 supplying the stimulus generator and lead/electrode assembly for the treatment and control of neuropsychiatric disorders.

19. The method of claim 18, wherein the selectively variable electrical parameters include pulse width, amplitude and frequency, sequence duration and intervals.

* * * * *